United States Patent
Samuelsson et al.

(10) Patent No.: US 7,312,067 B2
(45) Date of Patent: Dec. 25, 2007

(54) LACTIC ACID PRODUCING BACTERIA FOR USE AS PROBIOTIC ORGANISMS IN THE HUMAN VAGINA

(75) Inventors: Carolina Samuelsson, Uppsala (SE); Anna Weiner Jiffer, Laholm (SE); Endre Kvanta, Angelholm (SE)

(73) Assignee: Ellen AB, Angelholm (SE)

( * ) Notice: Subject to any disclaimer, the term of this patent is extended or adjusted under 35 U.S.C. 154(b) by 514 days.

(21) Appl. No.: 10/490,022

(22) PCT Filed: Sep. 19, 2002

(86) PCT No.: PCT/SE02/01704

§ 371 (c)(1),
(2), (4) Date: Apr. 8, 2004

(87) PCT Pub. No.: WO03/038068

PCT Pub. Date: May 8, 2003

(65) Prior Publication Data

US 2004/0253217 A1 Dec. 16, 2004

(30) Foreign Application Priority Data

Sep. 20, 2001 (SE) .................................... 0103127

(51) Int. Cl.
 *C12N 1/20* (2006.01)
 *A61F 13/15* (2006.01)
(52) U.S. Cl. .................... 435/252.9; 424/430; 424/431; 424/93.1; 424/93.45
(58) Field of Classification Search ............... 424/93.1, 424/93.4, 93.45, 430, 431; 435/252.9
See application file for complete search history.

(56) References Cited

U.S. PATENT DOCUMENTS 5,176,911 A * 1/1993 Tosi et al. ............... 424/93.45
5,645,830 A * 7/1997 Reid et al. ............... 424/93.45
6,093,394 A   7/2000 Chrisope
6,180,100 B1 * 1/2001 Bruce et al. ............. 424/93.45

FOREIGN PATENT DOCUMENTS

| EP | 0594628 B1 * | 2/1992 |
| EP | 0 956 858 | 11/1999 |
| WO | WO 92/13577 | 8/1992 |
| WO | WO 00/35465 | 6/2000 |

OTHER PUBLICATIONS

Soledad Boris, et al., "*Adherence of Human Vaginal Lactobacilli to Vaginal Epithelial Cells and Interaction with Uropathogens*", Infection and Immunity, May 1998, pp. 1985 to 1989 Vo. 66, No. 5.

Roger L. Cook et al., "*Effect of Culture Media and Growth Phase on the Morphology of Lactobacilli and on Their Ability to Adhere to Epithelial Cells*", Current Microbiology, vol. 17 (1988), pp. 159 to 166.

Gregor Reid et al., "*Identification and Plasmid Profiles of Lactobacillus Species From the Vagina of 100 Health Women*", FEMS Immunology and Medical Microbiology, vol. 15 (1996) pp. 23 to 26.

Eriksson et al., Acta Derm Venereol, vol. 85, No. 1, pp. 42-46 (2005).

Forsum, "Varning for Ellen!", Lakartidningen, vol. 101, No. 17, pp. 1544 (2004).

* cited by examiner

*Primary Examiner*—Ruth A Davis
(74) *Attorney, Agent, or Firm*—Birch, Stewart, Kolasch & Birch, LLP (57) ABSTRACT

The present invention discloses novel isolated strains of lactic acid producing bacteria of the genera *Lactobacillus* and *Pediococcus*, and a method for isolation of such bacterial strains, having the ability to colonise and become established in a human vagina, even during menstrual discharge. Furthermore, a composition comprising the bacterial strains and a sanitary article comprising the bacterial strains, such as a tampon, for prophylaxis and/or treatment of infections of the urogenital tract, are described. The present invention also describes a method for prophylaxis and/or treatment of infections of the urogenital tract, wherein at least one of the bacterial strains is administered vaginally.

6 Claims, 3 Drawing Sheets

LACTIC ACID PRODUCING BACTERIA FOR USE AS PROBIOTIC ORGANISMS IN THE HUMAN VAGINA

TECHNICAL FIELD

The present invention relates to lactic acid producing bacteria and use thereof.

TECHNICAL BACKGROUND

The normal microbial flora of the human vagina comprises lactic acid producing bacteria, which by tradition have been designated as Döderlein's bacilli.

Such lactic acid producing bacteria relate to non-sporeforming, Gram-positive bacteria producing lactic acid by fermentation of various sugars, such as glycogen and/or glucose.

Lactic acid producing bacteria comprise bacteria of, for instance, the genera *Lactobacillus, Leuconostoc, Pediococcus, Streptococcus, Lactococcus*, and *Enterococcus*.

Lactic acid producing bacteria may be divided into homofermentative and heterofermentative bacteria depending on their metabolic pathways. Homofermentative bacteria (e g *Lactobacillus acidophilus*) produce merely lactic acid, whereas heterofermentative bacteria also produce, for instance, carbon oxide, ethanol or acetic acid.

The genus *Lactobacillus* is a phenotypically heterogenous group of facultatively anaerobic, catalase-negative, rod-shaped lactic acid producing bacteria. Over 50 different species are recognised, and these species generally possess DNA with a low content of guanine (G) and cytosine (C), approximately 33-53%. The GC-content is constant within a species. Several species of *Lactobacillus* are found in humans, e g in the oral cavity, intestinal tract, and vagina. Species of *Lactobacillus* that are present in the vagina are, for instance, *Lactobacillus acidophilus, Lactobacillus fermentum, Lactobacillus gasseri, Lactobacillus crispatus, Lactobacillus casei* (sub-species rhamnosus), and *Lactobacillus jensenii*.

The genus *Pediococcus* is phenotypically a group of Gram-positive, catalase-negative, facultatively anaerobic, oxygen-tolerant, round-shaped (diameter about 0.6-1.0 μm), non-pathogenic, lactic acid producing bacteria.

Healthy, fertile women (about 15-60 years of age) present a pH of about 3.8-4.2 in the vagina between menses, primarily as a result of said lactic acid production. An acidic environment prevents vaginal establishment of, for instance, bacteria that are present in the colon, such as *Gardnerella vaginalis, Mobiluncus, Bacteroides, Prevotella* and *Eschericha coli*.

The skin of the urogenital tract and the urogenital mucus membranes of a healthy woman host a specific flora of beneficial and/or commensal microorganisms, such as various species of *Lactobacillus*. However, the urogenital tract can also be colonised by disease-causing microorganisms. The colonisation of unwanted microorgansims can be a result of sexual transmission, it can occur spontaneously or it can be the result of a disturbed normal microbial flora. The latter is, for instance, known to happen after certain antibiotic therapies.

Thus, the microbial flora of the female urogenital tract, such as in the vagina, may be disturbed and altered by a microbial infection, such as yeast (*Candida albinancs*), *Trichomonas vaginalis, Neisseria gonorrhoeae*, and *Chlamydia trachomatis*, and bacterial vaginosis (caracterized by increased prevalence of *Gardnerella vaginalis* and *Mobiluncus*), an antibiotic treatment or other often complex causes.

During menstruation and sexual intercourse, the pH in the vagina is increased by the addition of blood and sperm, respectively. These fluids contain a lot of proteins, which may be digested by bacteria (e g *Gardnerella vagnalis* and *Mobiluncus*), which, as previously disclosed, might be established in the vagina under conditions of increased pH. Degradation products, such as amines (e g putrescine and cadacerine) are then produced. At increased pH, these amines become volatile and present a "fishy" odour. Additionally, these women often have complaints of increased vaginal discharge and irritation. This condition is called bacterial vaginosis (BV), and is the most common condition associated with irritation and increased amount of odorous vaginal discharge (see Morris, M; Nicoll, A; Simms, I; Wilson, J; Catchpole, M, *Bacterial vaginosis*: A public health review, British Journal of Obstetrics and Gynaecology, 108(5): 439-450, May 2001).

*Bacterial vaginosis* is believed to be the result of displaced vaginal lactic acid producing bacteria which are replaced by a range of unwanted species such as *Gardnerella vaginalis, Bacterioides, Mobiluncus, Prevotella bivia*, and *Mycoplasma hominis*.

A method to diagnose bacterial vaginosis (BV) is described by Amsel Criteria. First, the pH of vaginal discharge is measured. The pH is elevated above 4.5 in about 90% of women with BV. Second, if 10% KOH is added to the vaginal discharge, a "fishy" odour will be released in about 70% of women with BV. Third, often the presence on wet mount of squamous epithelial cells covered with small *coccobacilli* ("clue cells") is observed. Another reliable test for BV is direct Gram stain of vaginal fluid. A standardised method for interpretation of Gram stains for BV was presented by Nugent et al. (See Example 1.)

It is known that lactic acid producing bacteria have an ability to inhibit the growth and/or reduce the pathogenicity of many of the pathogens associated with urogenital infections (see e g Redondo-Lopez, V; Cook, R L; Sobel, J D, Emerging role of lactobacillus in the control and maintenance of the vaginal bacterial microflora, Reviews of infectious diseases, vol 12, no 5, September-October 1990, and Boris, S; Barbes, C, Role played by *lactobacilli* in controlling the population of vaginal pathogens, Microbes and infection, vol 2, pp 543-546, 2000).

It is also known that the antagonistic properties of lactic acid producing bacteria against said pathogens are at least partially denoted by their ability of producing different antagonistic substances, such as lactic acid, hydrogen peroxide, bacteriocins, etc.

A healthy vagina is estimated to host between $10^8$-$10^9$ cfu (=colony-forming units) lactic acid producing bacteria. The composition of this flora is a result of which specific strains the woman has inherited from her mother and/or which strains have migrated from her digestive tract to the urogenital tract.

Prior art describes formulations, such as suspensions, suppositories and gelatine capsules, comprising viable lactic acid producing bacteria. Such formulations are for instance disclosed in U.S. Pat. No. 5,466,463 and WO 9 309 793.

Furthermore, it is known how to impregnate absorbent articles, such as tampons and sanitary napkins, with lactic acid producing bacteria for the purpose of preserving a normal microbial flora in the urogenital tract of women, and thereby preventing urogenital infections, or regenerating a normal microbial flora in the urogenital tract of women.

Such a product is disclosed in EP 0 594 628 and the Swedish patent application 0003544-4.

However, to obtain the above disclosed effect it is crucial that the uropathogen-inhibiting, lactic acid producing bacteria really colonise and establish in vivo, and actually remain in the vagina over more than one menstruation cycle upon vaginal administration.

Whether a bacterial strain will colonise the vagina or not is dependent on the adhesive properties of the specific bacterial strain as well as the hormonal, nutritional and acidity status of the vagina. Ongoing genital infection or treatment with antibiotics will also influence the ability of an introduced strain to colonise the vagina.

The menstrual cycle also affects the adherence, and maximum adherence occurs prior to ovulation and prior to menstrual discharge (U.S. Pat. No. 6,180,100 and Chan et al, Journal of Urology, March 1984). Thus, the most difficult time for administered lactic acid producing bacteria to colonise and establish in the vagina is during menstrual discharge.

With regard to colonisation and establishment of lactic acid producing bacteria in vivo, there might be a considerable disparity between clinical results and supposed bacterial behaviour from interpretation of in vitro analysis results. It is common that interactions between different bacterial species occur in the vagina, and this interaction pattern is difficult to recreate in the laboratory. Thus, even if a bacterial species display promising in vitro results, it might not establish in vivo and provide the desired therapeutic effect, i e to prevent, alleviate the effects of, and/or treat a microbial infection of the urogenital tract.

Furthermore, it is of great importance that the bacteria display stability of its genetic profile both upon repeated cultivation in large-scale production and for longer periods in vivo.

Another criterion that has to be fulfilled to produce an acceptable consumption product that provide the desired therapeutic effect, is the preservation of bacterial viability upon lyophilisation of the bacteria and upon storage of the lyophilised bacteria (i e, shelf life).

SUMMARY OF THE INVENTION

The present invention discloses novel isolated bacterial strains of the genera *Lactobacillus* and *Pediococcus*, which have an ability to colonise and become established in a human vagina upon vaginal administration, even during menstrual discharge, of at least one of the bacterial strains. The bacteria are considered established if the bacteria are still present in the vagina after at least two menstrual cycles from the time of administration.

It is an advantage that the bacterial strains according to the invention display an ability to establish during menstrual discharge since the bacteria then may be easily administered using, for instance, a tampon impregnated with said bacteria.

Established lactic acid producing bacteria of said strains prevent, alleviate the effects of, and/or treat a microbial infection of the urogenital tract, in particular bacterial vaginosis. To obtain these therapeutic effects, it is essential that the bacteria really establish upon administration, and thus, are still present in the vagina even after several menstrual discharges.

Said bacterial strains have been deposited according to the Budapest Agreement at the BCCM/LMG (Belgian Coordinated Collections of Microorganisms/Laboratorium voor Microbioligie-Bacteriënverzammeling, Universiteit Gent) in Belgium on Jun. 14 2001, and comprise the strain of *Lactobacillus gasseri*, denoted by the applicant as LN 40, deposited under number LMG P-20560, the strain of *Lactobacillus casei* subsp *rhamnosus*, denoted by the applicant as LN 113, deposited under number LMG P-20562, the strain of *Lactobacillus fermentum*, denoted by the applicant as LN 99, deposited under number LMG P-20561, the strain of *Lactobacillus crispatus*, denoted by the applicant as LN 01, deposited under number LMG P-20558, and the strain of *Pediococcus acidilactici*, denoted by the applicant as LN 23, deposited under number LMG P-20559, or variants thereof having essentially corresponding phenotypic and/or genotypic characteristics.

Furthermore, the present invention describes a method for isolation of a bacterial strain of the genus *Lactobacillus* or *Pedicoccus* having the ability to colonise and become established in a human vagina, wherein a) a bacterial sample, such as vaginal fluid, is collected from the vaginal tract of a woman with a normal, healthy vaginal flora of microorganisms, b) lactic acid producing bacteria are selected from the vaginal sample of step a), c) the lactic acid producing bacteria of step b) are pure cultured in vitro in a suitable nutrient medium providing at least one isolated bacterial strain, d) at least one pure cultured bacterial strain of step c) and/or a combination of at least two bacterial strains of step c) is evaluated as to its ability to colonise and become established in the vagina upon vaginal administration of the bacterial strain to a woman during her menstrual discharge, said woman displaying a disturbed vaginal flora of microorganisms, wherein said bacterial strain or strains is/are considered established if the bacterial strain or strains is/are still present in the vagina after at least two menstrual-cycles from the time of administration, and e) at least one bacterial strain of step d) that display said ability to colonise and become established in the vagina is selected.

Preferably, at least one pure cultured bacterial strain of step c), and/or a combination of at least two bacterial strains of step c), is lyophilised.

Furthermore, this/these strain/strains is/are preferably evaluated and selected as to stability of bacterial viability upon lyophilisation and viability of lyophilised bacteria over long periods of storage, wherein said bacterial viability is considered stable if at least 40% of the bacteria have a preserved viability upon lyophilisation and storage of the lyophilised bacteria at about −18° C. for at least 12 months.

In addition, this/these strain/strains is/are preferably evaluated and selected as to genetic stability upon repeated cultivation and in vivo upon vaginal administration, wherein said bacteria are considered as genetically stable if their genetic profile is preserved in vivo for at least 12 months.

The present invention also discloses a bacterial strain of the genus *Lactobacillus* or *Pediococcus* having the ability to colonise and become established in a human vagina during menstrual discharge, wherein the strain can be isolated according to the above described method. Such bacterial strains are preferably the strain of *Lactobacillus gasseri*, denoted by the applicant as LN 40, deposited under number LMG P-20560, the strain of *Lactobacillus casei* subsp *rhamnosus*, denoted by the applicant as LN 113, deposited under number LMG P-20562, the strain of *Lactobacillus fermentum*, denoted by the applicant as LN 99, deposited under number LMG P-20561, the strain of *Lactobacillus crispatus*, denoted by the applicant as LN 01, deposited under number LMG P-20558, and the strain of *Pediococcus acidilactici*, denoted by the applicant as LN 23, deposited under number LMG P-20559, or variants thereof having essentially corresponding phenotypic and/or genotypic characteristics.

In addition, the present invention describes a composition for prophylaxis and/or treatment of infections of the urogenital tract, comprising at least one of said bacterial strains (LN 40, LN 113, LN 99, LN 01, and LN 23).

Preferably, the composition comprises all said strains, i e strain LN 40, strain LN 113, strain LN 99, strain LN 01, and strain LN 23.

It is known in the art that a combination of different bacteria abbreviates the generation time of a bacterium, resulting in a more rapid bacterial growth. Furthermore, since different species of lactic acid producing bacteria have different fermentation patterns and characteristics, it is preferable to use a combination of different bacterial species.

A combination of all said strains according to the invention, i.e. LN 40, LN-113, LN 99, LN 01, and LN 23, displays an even better inhibition of uropathogens than each of said strains taken alone.

The composition is preferably formulated for vaginal administration, such as a suppository, capsule, pills, tablet, suspension, spray, gel, cream, powder, or any other form of vaginal insert.

Additionally, the present invention describes a sanitary article, such as a feminine absorbent product (e g tampon, sanitary napkin, panty liner), a diaper, and an incontinence guard, for prophylaxis and/or treatment of infections of the urogenital tract comprising at least one of said bacterial strains (LN 40, LN 113, LN 99, LN 01, and LN 23).

Preferably, the sanitary article comprises all said strains, i e strain LN 40, strain LN 113, strain LN 99, strain LN 01, and strain LN 23, for the same reasons as given above concerning the composition.

The sanitary article is preferably a tampon.

Furthermore, the present invention describes the use of at least one of said bacterial strains (LN 40, LN 113, LN 99, LN 01, and LN 23) for the production of a composition or a sanitary article for prophylaxis and/or treatment of infections of the urogenital tract, preferably bacterial vaginosis or any other bacterial disorder in the vagina.

Moreover, the present invention describes a method for prophylaxis and/or treatment of infections of the urogenital tract, preferably bacterial vaginosis or any other bacterial disorder in the vagina, wherein at least one of said bacterial strains (LN 40, LN 113, LN 99, LN 01, and LN 23) is vaginally administered in a therapeutically effective amount to prevent, alleviate the effects of, and/or treat a microbial infection.

Other features and advantages of the present invention will become apparent from the following detailed description of the invention.

DETAILED DESCRIPTION OF THE INVENTION

As used herein the term "lactic acid producing bacteria" means bacteria that by fermentation produce lactic acid.

As used herein the term "therapeutically effective amount" means an amount that will lead to the desired therapeutic effect.

The desired therapeutic effect is prophylaxis and/or treatment of infections of the urogenital tract, such as bacterial vaginosis or any other bacterial disorder in the vagina.

As used herein the term "isolated bacterial strain" means that the strain might be cultivated in vitro in a culture comprising said strain.

As used herein the term "bacterial sample" means a sample comprising bacteria. The sample might, for instance, be vaginal fluid/discharge.

As used herein the term "normal, healthy vaginal flora of microorganisms" means that the woman has no vaginal complaints, and that the Gram stain of the vaginal sample gives a total score of 0-3 according to the method presented by Nugent et al (see Example 1).

As used herein the term "disturbed vaginal flora of microorganisms" means that the woman has some vaginal complaints, such as increased vaginal discharge and/or "fishy" vaginal odour. Furthermore, the Gram stain of the vaginal sample gives a total score of at least 4, in particular $\geq 7$, according to the method presented by Nugent et al (see Example 1).

As used herein the term "suitable nutrient medium" means a medium, such as LAB broth or MRS broth, in which the bacteria might be cultivated.

As used herein the term "sanitary article" means tampons (both digital tampons and tampons with an applicator), sanitary napkins, panty liners, diapers, incontinence guards and the like.

The present invention discloses novel isolated strains of lactic acid producing bacteria of the genera *Lactobacillus* and *Pediococcus*, which have an ability to colonise and become established in a human vagina upon vaginal administration, even during menstrual discharge, of at least one of the bacterial strains. The bacteria are considered established if the bacteria are still present in the vagina after at least two menstrual cycles from the time of administration.

Said bacterial strains have been deposited according to the Budapest Agreement at the BCCM (Belgian Coordinated Collections of Microorganisms) in Belgium on 14 Jun. 2001, and comprise the strain of *Lactobacillus gasseri*, denoted by the applicant as LN 40, deposited under number LMG P-20560, the strain of *Lactobacillus casei* subsp *rhamnosus*, denoted by the applicant as LN 113, deposited under number LMG P-20562, the strain of *Lactobacillus fermentum*, denoted by the applicant as LN 99, deposited under number LMG P-20561, the strain of *Lactobacillus crispatus*, denoted by the applicant as LN 01, deposited under number LMG P-20558, and the strain of *Pediococcus acidilactici*, denoted by the applicant as LN 23, deposited under number LMG P-20559, or variants thereof having essentially corresponding phenotypic and/or genotypic characteristics.

Furthermore, the present invention describes a method for isolation of a bacterial strain of the genus *Lactobacillus* or *Pedicoccus* having the ability to colonise and become established in a human vagina, wherein a) a bacterial sample, such as vaginal fluid, is collected from the vaginal tract of a woman with a normal, healthy vaginal flora of microorganisms, b) lactic acid producing bacteria are selected from the vaginal sample of step a), c) the lactic acid producing bacteria of step b) are pure cultured in vitro in a suitable nutrient medium providing at least one isolated bacterial strain, d) at least one pure cultured bacterial strain of step c) and/or a combination of at least two bacterial strains of step c) is evaluated as to its ability to colonise and become established in the vagina upon vaginal administration of the bacterial strain to a woman during her menstrual discharge, said woman displaying a disturbed vaginal flora of microorganisms, wherein said bacterial strain or strains is/are considered established if the bacterial strain or strains is/are still present in the vagina after at least two menstrual cycles from the time of administration, and e) at least one bacterial strain of step d) that display said ability to colonise and become established in the vagina is selected.

Preferably, at least one pure cultured bacterial strain of step c), and/or a combination of at least two bacterial strains of step c), is lyophilised.

An essential amount of the bacteria should be viable after lyophilisation and then preserve viability upon storage. Furthermore, an essential amount of lyophilised bacteria formulated in, for instance, compositions and/or sanitary articles for commercial sale should preserve viability upon storage at room temperature.

Thus, said strain/strains is/are preferably evaluated and selected as to stability of bacterial viability upon lyophilisation and viability of lyophilised bacteria over long periods of storage, wherein said bacterial viability is considered stable if at least 40% of the bacteria have a preserved viability upon lyophilisation and storage of the lyophilised bacteria at about −18° C. for at least 12 months.

Furthermore, at least 1% of the lyophilised bacteria formulated in some kind of preservation matrix, such as an oil, and enclosed in a composition and/or a sanitary article should preserve viability for at least 12 months at room temperature.

Furthermore, an important characteristic is the stability of the bacterial genetic profile upon repeated cultivation in large-scale production, and during manufacturing processes of, for instance, compositions and sanitary articles. The bacteria should preferably preserve their genetic profile upon at least 10 repeated cultivation. Furthermore, the bacteria should display genetic stability in vivo for longer periods after administration, such as at least 12 months. Thus, said strain/strains is/are preferably evaluated and selected as to genetic stability in vivo upon vaginal administration, wherein said bacteria are considered as genetically stable if their genetic profile is preserved in vivo for at least 12 months. Moreover, the bacterial growth and generation time is also essential. Vaginally administered lyophilised bacteria should start to grow within at least 4 hours from the time of administration. The generation time should be less than 2 h.

The present invention also discloses a bacterial strain of the genus *Lactobacillus* or *Pedicoccus* having the ability to colonise and become established in a human vagina during menstrual discharge, wherein the strain can be isolated according to the above described method. Such bacterial strains are preferably the strain of *Lactobacillus gasseri*, denoted by the applicant as LN 40, deposited under number LMG P-20560, the strain of *Lactobacillus casei* subsp *rhamnosus*, denoted by the applicant as LN 113, deposited under number LMG P-20562, the strain of *Lactobacillus fermentum*, denoted by the applicant as LN 99, deposited under number LMG P-20561, the strain of *Lactobacillus crispatus*, denoted by the applicant as LN 01, deposited under number LMG P-20558, and the strain of *Pediococcus acidilactici*, denoted by the applicant as LN 23, deposited under number LMG P-20559, or variants thereof having essentially corresponding phenotypic and/or genotypic characteristics.

Isolation and evaluation of *Lactobacillus* and *Pediococcus* strains

Bacterial strains of the genera *Lactobacillus* and *Pediococcus* having the ability to colonise and become established in a human vagina, were isolated in accordance with the following steps:

vaginal fluid was collected from the vaginal tract of a woman with a normal, healthy vaginal flora of microorganisms, lactic acid producing bacteria (about 25 different strains) were selected from the vaginal fluid by placing a smear of said fluid on MRS agar selective for lactic acid producing bacteria (single colonies were picked and plated onto fresh MRS agar for control of purity), the lactic acid producing bacteria were then pure cultured in vitro in a suitable nutrient medium, and under suitable conditions (pH, temperature, etc) providing isolated bacterial strains, and the pure cultured bacterial strains were thereafter evaluated as to its ability to colonise and become established in the vagina upon vaginal administration of the bacterial strains to a woman during her menstrual discharge, said woman displaying a disturbed vaginal flora of microorganisms.

LN 40 was pure cultured in LAB broth (about pH 6.5) micro-aerofilic at about 37° C.

LN 113 was pure cultured in MRS broth (about pH 6.5) micro-aerofilic at about 37° C.

LN 99 was pure cultured in LAB broth (about pH 6.5) micro-aerofilic at about 37° C.

LN 01 was pure cultured in MRS broth (about pH 6.5) anaerobic at about 37° C.

LN 23 was pure cultured in MRS broth (about pH 6.5) micro-aerofilic at about 37° C.

The pure cultured bacterial strains were first evaluated with regard to generation time. Those bacterial strains (about 15 different strains) that showed a generation time<30 minutes were selected. These selected strains were screened on the basis of their ability to inhibit growth of some microorganisms in vitro (data not shown). First, the ability to inhibit growth of *Staphilococcus epidemidis* (two different strains), *Enterococcus cloace*, *Eschericha coli*, *Serratia marcesus*, *Micrococcus lysodeicticus*, and *Candida albicans* was evaluated. 8 different bacterial strains (7 strains of the genus *Lactobacillus* and 1 strain of the genus *Pediococcus*) showed this ability, and were thus selected. These 8 strains were further evaluated as to the ability to inhibit growth of the uropathogen *Gardernella vaginalis*. The best strains (i e the strains having best potential to colonise a disturbed vaginal flora of microorganisms) was LN 40, LN 113, LN 99, LN 01, and LN 23.

These strains were further evaluated by means of clinical studies, wherein the bacteria were considered established in the vagina if the bacteria were still present in the vagina after at least two menstrual cycles from the time of administration (the administration of bacteria started during the first menstrual discharge). Those bacterial strains (LN 40, LN 113, LN 99, LN 01, and LN 23) that displayed said ability to colonise and become established in the vagina were selected.

Additionally, stability of bacterial viability upon lyophilisation and viability of lyophilised bacteria over long periods of storage (shelf life), preservation of genetic profile upon repeated cultivation and in vivo, and bacterial growth process were evaluated.

EXAMPLE 1

Colonisation and Establishment of Lactic Acid Producing Bacteria upon Vaginal Administration 15 BV-patients (women which had been diagnosed having *Bacterial Vaginosis*) were studied. All 15 patients were treated with clindamycin ovules (Dalacin® 2% ovule, from Pharmacia) for 3 days. Thereafter the treatment continued with a double blind placebo controlled part where 6 patients used tampons comprising approximately $10^3$ cfu lyophilised bacteria of the strains LN 01, LN 23, LN 99, LN 113, and LN 40 during the first menstrual period after the antibiotic treatment. The other 9 patients used conventional tampons without lactic acid producing bacteria. During the second menstrual period, all 15 patients used conventional tampons without lactic acid producing bacteria, and a vaginal sample was taken a few days after this menstruation.

The vaginal samples were Gram stained. In the standardised Gram stain method presented by Nugent et al, the presence or absence of certain bacterial morphotypes is analysed. The morphotypes are large, Gram-positive bacillus of the *Lactobacillus morphotype*; smaller *Gramvariable bacilli* called the *Gardnerella morphotype*; and curved rods. The organisms present in the vaginal fluid are quantified, and transferred to a score (se Table 1).

TABLE 1

| | Code | | |
|---|---|---|---|
| *Lactobacillus* morphotype | *Gardnerella* and Bacteroides morphotypes | Curved Gram-variable rod | Score |
| 4+ | 0 | 0 | 0 |
| 3+ | 1+ | 1+ or 2+ | 1 |
| 2+ | 2+ | 3+ or 4+ | 2 |
| 1+ | 3+ | | 3 |
| 0 | 4+ | | 4 |

Codes 0 to 4+ are based on the average number of organisms with that morphotype per oil immersion field; 1+, <1 present; 2+, 1-4 present; 3+, 5-30 present; 4+, >30 present. A total score is obtained by summarising the scores for all three morphotypes. The total score is interpreted as follows: 0-3, normal; 4-6, intermediate; and ≧7, BV.

TABLE 2

| Patient no | Gram stain before study start | Tampons (L = lactic acid producing bacteria) | Gram stain after the second menstrual period |
|---|---|---|---|
| 1 | 7 | L | 0 |
| 2 | 8 | L | 0 |
| 3 | 9 | | 7 |
| 4 | 5 | | 4 |
| 5 | 10 | | 0 |
| 6 | 8 | | 4 |
| 7 | 8 | L | 0 |
| 8 | 9 | | 4 |
| 9 | 4 | L | 0 |
| 10 | 8 | | 4 |
| 11 | 8 | | 4 |
| 12 | 8 | | 0 |
| 13 | 8 | L | 1 |
| 14 | 0 | | 5 |
| 15 | 9 | L | 0 |

*Bacterial Vaginosis* was not detected in the 6 patients that used the tampon with the lactic acid producing bacteria. Furthermore, the results show that the lactic acid producing bacteria were still present in the vagina after the second menstrual cycle.

Furthermore, these results show that a relatively small number of administered bacteria (approximately $10^3$ cfu) are enough for a complete vaginal colonization and establishment during menstrual discharge of the bacterial strains according to the present invention.

Additionally, the bacterial strains according to the present invention have excellent adhesive properties to the vaginal mucous membranes.

EXAMPLE 2

Colonisation and Establishment of Lactic Acid Producing Bacteria upon Vaginal Administration Four healthy women with no vaginal complaints used tampons comprising approximately $10^3$ cfu lyophilised bacteria of the strains LN 01, LN 23, LN 99, LN 113, and LN 40 during their monthly menstrual discharge during a period of 12-18 months.

Vaginal samples from each of the women were evaluated after said test period. The *Lactobacillus* and *Pediococcus* strains found in the samples were identified using RAPD (Random Amplified Polymorphic DNA) as described in Example 10.

LN 01 and LN 113 were identified in two of the vaginal samples from said women.

LN 40 was identified in one of the vaginal samples from said women.

LN 23 and LN 99 were not identified in any of the vaginal samples from said women.

An explanation for these results might be that, when said bacteria pool is administered to a woman displaying a healthy vaginal flora with a normal vaginal pH, LN 23 will not grow substantially. However, when said bacteria pool is administered to a woman displaying a disturbed vaginal flora of microorganisms, LN 23 will initially establish and provide a favourable environment for the other bacterial strains (LN 01, LN 113, LN 40, and LN 99) to grow in.

It shall also be noted that individually differences exist with regard to the suitability of a specific strain, and/or specific combinations of strains, to establish and grow in a woman's vagina.

At least one of said bacterial strains according to the invention was identified in each vaginal sample.

EXAMPLE 3

Stability of Viability upon Lyophilisation and Over Long Periods of Storage (Shelf Life) for Bacterial Strains LN 40, LN 113, LN 99, and LN 23

Lyophilised bacterial strains LN 40, LN 113, LN 99, and LN 23 were evaluated with regard to stability of viability over longer periods of storage (i e shelf life) at about −18° C.

TABLE 3

| Time after lyophilisation [months] | Viable bacteria [cfu/g] | | | | |
|---|---|---|---|---|---|
| | LN 40 | LN 113 | LN 99 | LN 23 | LN 01 |
| 0 | $83 \times 10^9$ | $224 \times 10^{10}$ | $33 \times 10^9$ | $290 \times 10^9$ | $20 \times 10^9$ |
| 12 | $47 \times 10^9$ (~57%) | $192 \times 10^{10}$ (~86%) | $14 \times 10^9$ (~42%) | $272 \times 10^9$ (~94%) | $19 \times 10^9$ (~95%) |
| 78 | $22 \times 10^9$ (~27%) | $46 \times 10^9$ (~21%) | $6 \times 10^9$ (~18%) | $155 \times 10^9$ (~53%) | $2 \times 10^9$ (~10%) |

The results presented in Table 3 show that at least 40% of the bacteria are still viable after 12 months at −18° C. Furthermore, at least about 10-20% of the bacteria are still viable after 78 months at −18° C.

Furthermore, these bacteria were also analysed according to API 50CH, and results obtained from this analysis indicated that the strains LN 40, LN 113, LN 99, LN 23, and LN 01 preserve their genetic profile for at least 78 months during storage in lyophilised form at −18° C.

Lyophilised bacteria (LN 40, LN 113, LN 99, and LN 23) were dispersed in Akosoft® 36 (from Karlshamns AB) and evaluated with regard to stability of viability over longer periods of storage (i e shelf life) at about 8° C and 22° C., respectively.

TABLE 4

| Time after preparation [week/months] | Viable bacteria [cfu/g] | |
|---|---|---|
| | +8° C. | +22° C. |
| 0 | $3.5 \times 10^{10}$ | $3.5 \times 10^{10}$ |
| 1 week | $2.7 \times 10^{10}$ (~75%) | $1.9 \times 10^{10}$ (~53%) |
| 1 | $2.5 \times 10^{10}$ (~71%) | $1.3 \times 10^{10}$ (~37%) |
| 3.5 | $2.0 \times 10^{10}$ (~55%) | $6 \times 10^9$ (~17%) |
| 6 | $2.4 \times 10^{10}$ (~68%) | $3.9 \times 10^9$ (~11%) |
| 9 | $1.8 \times 10^{10}$ (~50%) | $1.0 \times 10^9$ (~2.8%) |
| 12 | $1.7 \times 10^{10}$ (~49%) | $1.3 \times 10^9$ (~3.7%) |

The results presented in Table 4 show that about 45-50% of the bacteria are still viable after 12 months at 8° C. Furthermore, about 4% of the bacteria are still viable after 12 months at room temperature, i e 22° C.

Similar results were obtained for a lyophilised bacteria pool comprising all bacterial strains according to the invention, including LN 01.

EXAMPLE 4

Preservation of Genetic Profile upon Repeated Cultivation for Bacterial Strains LN 40, LN 113, LN 99, LN 01, and LN 23

The bacterial strains (LN 40, LN 113, LN 99, LN 01, and LN 23) were repeatedly cultivated 10 times and thereafter evaluated with API 50CH. The fermentation pattern of each bacterial strain (see example 9) were preserved after the repeated cultivation. Thus, the results indicated that said bacterial strains preserve their genetic profile upon repeated cultivation.

EXAMPLE 5

Bacterial Growth Process for Bacterial Strains LN 40, LN 99, LN 113, LN 23, and LN 01

To provide said desired therapeutic effect, vaginally administered lyophilised bacteria should start to grow in the vagina within at least 4 hours from the time of administration.

The absorbency (optical density, OD) was measured at 620 nm for lyophilised bacteria (LN 40, LN 113, LN 99, LN 23, and LN 01) added to sterilised MRS broth. Two types of experiments (see FIGS. 1a and 1b) were performed:
  a) 0.01 g lyophilised bacteria were added to 3 ml MRS broth, and 100 µl of this dispersion was diluted with 3 ml additional MRS broth, and
  b) lyophilised bacteria were added to MRS broth in an amount which resulted in an absorbency of approximately 0.100.

The cuvettes containing the above bacteria dispersions were placed at 37° C. and the absorbency was measured every 15-min for 10.5 h.

Figure 1A:
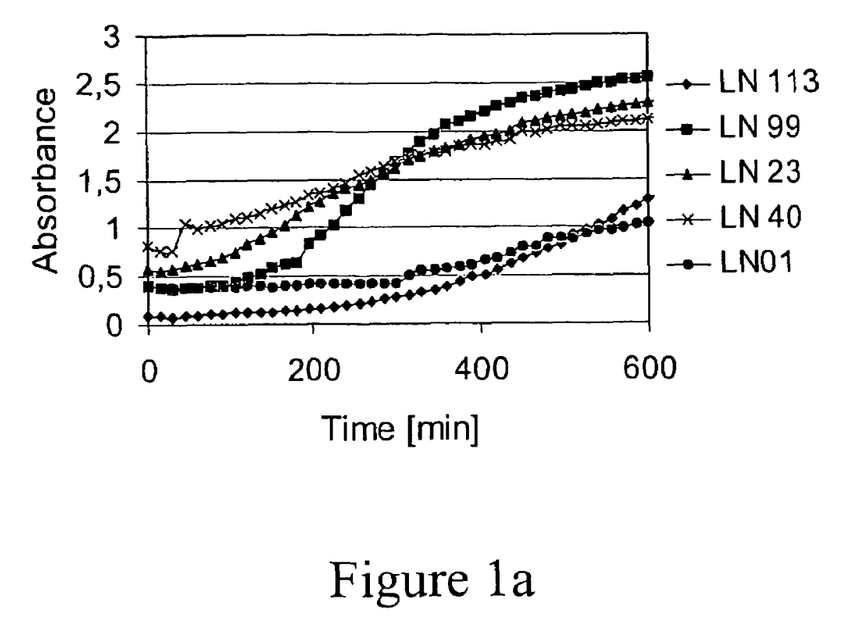
FIG. 1a and 1b show the growth process of bacterial strains LN 40, LN 99, LN 113, and LN 23, respectively.
Figure 1B:
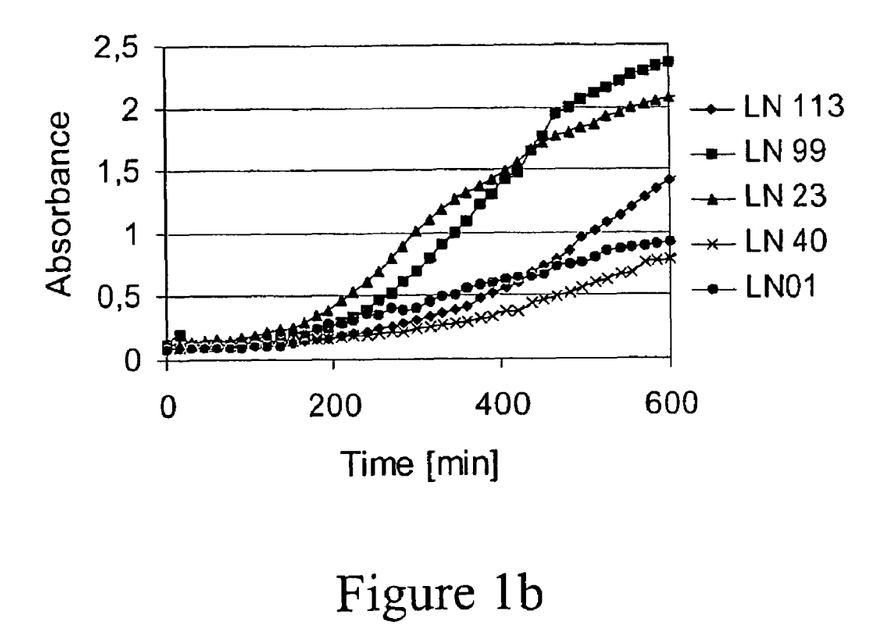

As can be seen in FIG. 1a and 1b, the bacterial growth for each bacterial strain (LN 40, LN 113, LN 99, LN 23, and LN 01, respectively) is rapid, and all bacterial strains start to grow within at least 2 hours.

Furthermore, the generation time of each bacterial strain is about 20-25 min. Thus, the bacteria grow faster than uropathogens, which is very favourable in view of the herein described use of the bacteria.

In addition, it is known in the art that a combination of different bacteria may abbreviate the generation time of a bacterium, resulting in even more rapid bacterial growth. Furthermore, since different species of lactic acid producing bacteria have different fermentation patterns and characteristics, it is preferable to use a combination of different bacterial species.

It shall be noted that a combination of freeze-dried LN 40, LN 99, LN 113, LN 23, and LN 01 start to grow within 1.5 h, thus at least 25% faster than the time required for each bacterial strain.

EXAMPLE 6

Ability to Inhibit Growth of Uropathogens

The purpose of this example is to show that a bacteria pool of LN 40, LN 113, LN 99, LN 23, and LN 01 is even more effective with regard to inhibiting growth of uropathogens than each of the bacterial strains taken alone.

Figure 3:
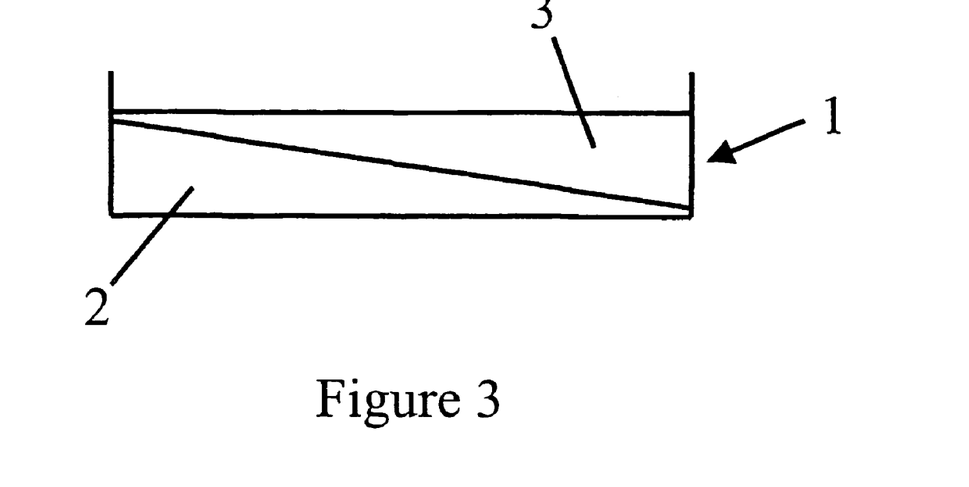
FIGS. 3 and 4 show the experimental set-up used in Example 6.

The lactic acid producing bacteria to be tested was homogeneously added to a melted sterile, buffered agar medium, such as MRS agar. The mixture obtained was poured into a Petri dish (Ø 90 mm) 1 and the dish was tilted in such a way that the agar mixture 2 only reached about 1 mm from the bottom of the dish at one side of the dish and about 11 mm at the opposite side of the dish, as shown in FIG. 3.

The uropathogen was homogeneously added to a melted sterile, buffered agar medium, such as VRB (Violet-Red Bile) agar. This mixture was poured on top of the above disclosed solidified agar comprising said lactic acid bacteria, as shown in FIG. 3, and this agar mixture 3 was also allowed to solidify.

Figure 4:
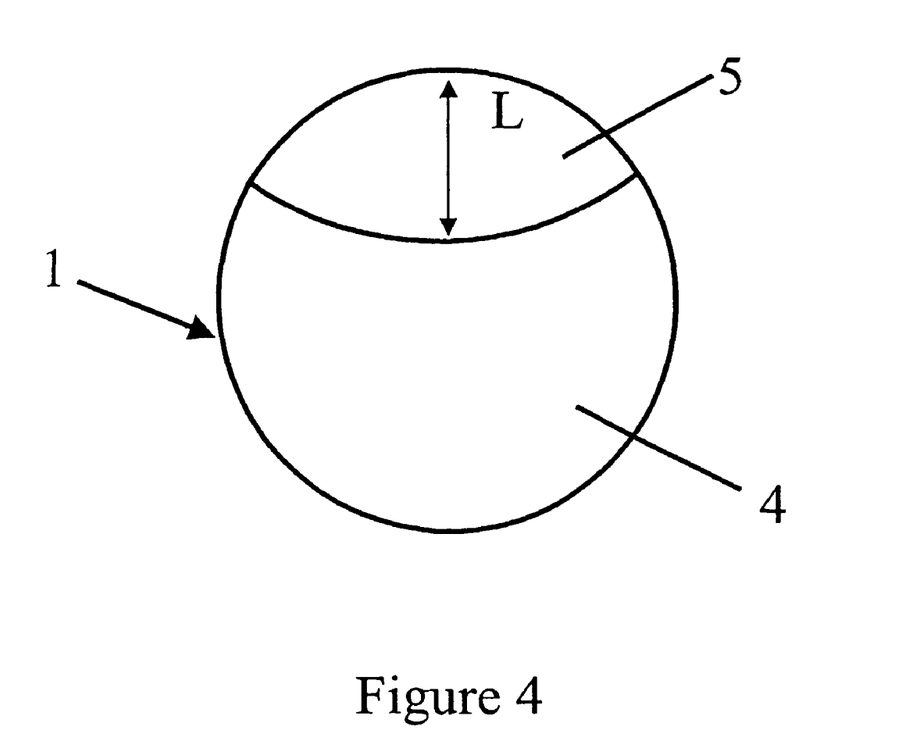

The lactic acid bacteria and the uropathogen were thereafter incubated at 37° C. for about 24 h. Two distinct zones, 4 and 5, were then seen in the dish 1 from above, as shown in FIG. 4. In the first zone 4, the uropathogen had been able to grow. In the second zone 5, the lactid acid bacteria had inhibited growth of the uropathogen.

The ability of the lactic acid bacteria to inhibit the uropathogen can be quantified by measuring the length L of the second zone 5, i.e. the inhibited growth zone 5.

An enteropathogen *E coli* (EPEC) strain was used in this experiment.

The length L of the inhibited growth zone was within the range from 8 to 22 mm for each of the bacterial strains LN 40, LN 113, LN 99, LN 01, and LN 23.

However, the bacteria pool comprising LN 40, LN 113, LN 99, LN 01, and LN 23 gave a length L of the inhibited growth zone of 32-34 mm.

Thus, a bacteria pool comprising all of the bacterial strains LN 40, LN 113, LN 99, LN 01, and LN 23 is even more effective than each bacterial strain taken alone for inhibiting the growth of uropathogens, such as *E coli*. Hence, it is preferable to use a combination of said bacterial strains according to the invention.

Characterisation of Bacterial Strains LN 40, LN 113, LN 99, LN 01, and LN 23

The bacteria were characterised by both phenotypic and genotypic methods.

EXAMPLE 7

Microbiological Characterisation of Bacterial Strains LN 40, LN 113, LN 99, LN 01, and LN 23

The strains (LN 40, LN 113, LN 99, LN 23, and LN 01) were characterised with regard to cell morphology, Gram stain, oxidase and catalase reaction.

The strain LN 40 comprised Gram-positive, catalase-negative, oxidase-negative, non-spore-forming, rod-shaped (about 0.9 μm×3-10 μm) bacteria, which occurred as single cells or in pairs.

The strain LN 99 comprised Gram-positive, catalase-negative, oxidase-negative, non-spore-forming, rod-shaped (about 0.9 μm×1.5-2.0 μm) bacteria, which occurred as single cells.

The strain LN 113 comprised Gram-positive, catalase-negative, oxidase-negative, non-spore-forming, rod-shaped (about 0.9 μm×2 μm) bacteria, which occurred as single cells or in pairs.

The strain LN 01 comprised Gram-positive, catalase-negative, oxidase-negative, non-spore-forming, straight or slightly curved rod-shaped (about 0.8-1.6 μm×2.3-11 μm) bacteria, which occurred as single cells or in chains.

The strain LN 23 comprised Gram-positive, catalase-negative, oxidase-negative, non-spore-forming, round-shaped (Ø about 1 μm) bacteria, which occurred as single cells or in pairs.

EXAMPLE 8

SDS-PAGE and Cluster Analysis of Bacterial Strains LN 40, LN 113, LN 99, LN 01, and LN 23

Cultures were grown on MRS agar (Oxoid CM361) for 24 h at 370° C. under anaerobic conditions. The preparation of cell extracts and the protein gel electrophoresis (SDS-PAGE) were carried out at BCCM™/LMG in conformity with the protocol established by the Research Group of Laboratory for Microbiology, University Ghent (Pot, B, Vandamme, P, Kersters, K, Analysis of elctrophoretic whole-organism protein fingerprints, Chemical Methods in Prokaryotic Systematics, M, Goodfellow, and A G, O'Donell (eds), J Wiley & Sons, Chichester (1994)).

The normalised and digitised protein patterns were numerically analysed and clustered with the reference profiles in the BCCM database (December 1999) for LN 40, LN 113, LN 99, and LN 23. LN 01 was analysed and clustered with the reference profiles in the CCUG database (January 2001).

The strain LN 40 was found to belong to the species *Lactobacillus johnsonii* or *Lactobacillus gasseri*.

The strain LN 99 was found to belong to the species *Lactobacillus fermentum*.

The strain LN 113 was found to belong to the species *Lactobacillus casei* subsp *rhamnosus*.

The strain LN 23 was found to belong to the species *Pediococcus acidilactici*.

The strain LN 01 was found to belong to the species *Lactobacillus crispatus*.

EXAMPLE 9

Characterisation of Bacterial Strains LN 40, LN 113, LN 99, LN 23 and LN 01 using API 5OCH and Rapid ID32 Strep The ability of the strains (LN 40, LN 113, LN 99, LN 23 and LN 01) to ferment different carbohydrates is shown in Table 5. The tests were carried out by means of API 50CH and API rapid ID32strep at 37° C. in accordance with the manufacturer's instructions. For those results that differ between API 50CH API and rapid ID32strep, the API 50CH result is considered more reliable.

The resulting fermentation patterns were searched for in the CCUG database. The highest database score obtained for each strain confirmed the results from the above-described analysis (SDS-PAGE/cluster analysis) with regard to which respective bacterial species said strains are belonging.

Furthermore, the reaction with rhamnose confirmed that the strain LN 113 belongs to the species *Lactobacillus casei* subsp *rhamnosus*.

However, comparisons between LN 40, LN 99, LN 113, LN 23 and LN 01, respectively, and type strains of each bacterial species (CCUG 31451$^T$, CCUG 30138$^T$, CCUG 21452$^T$, CCUG 32235$^T$, and, CCUG 44117$^T$, respectively) showed significant differences for all strains (LN 40, LN 113, LN 99, LN 23, and LN 01) with regard to fermentation patterns.

In Table 5, 1 denotes that no reaction occurred, 2 denotes the occurrence of a vague reaction, 3 denotes the occurrence of a reaction, 4 denotes the occurrence of a strong reaction, and 5 denotes the occurrence of a very strong reaction.

TABLE 5

|  | LN 40 | LN 99 | LN 113 | LN 23 | LN 01 |
|---|---|---|---|---|---|
| API 50CH |  |  |  |  |  |
| Control | 1 | 1 | 1 | 1 | 1 |
| Glycerol | 1 | 1 | 1 | 1 | 1 |
| Erythritol | 1 | 1 | 1 | 1 | 1 |
| D-arabinose | 1 | 1 | 1 | 1 | 1 |
| L-arabinose | 1 | 1 | 1 | 5 | 1 |
| Ribose | 1 | 5 | 5 | 5 | 1 |
| D-xylose | 1 | 5 | 1 | 5 | 1 |
| L-xylose | 1 | 1 | 1 | 1 | 1 |
| Adonitol | 1 | 1 | 1 | 1 | 1 |
| β-methyl-D-xyloside | 1 | 1 | 1 | 1 | 1 |
| Galactose | 4 | 5 | 5 | 5 | 3 |
| Glucose | 5 | 5 | 5 | 5 | 5 |
| Fructose | 5 | 4 | 5 | 5 | 5 |
| Mannose | 4 | 3 | 5 | 5 | 4 |
| Sorbose | 1 | 1 | 5 | 1 | 1 |
| Rhamnose | 1 | 1 | 3 | 1 | 1 |
| Dulcitol | 1 | 1 | 1 | 1 | 1 |
| Inositol | 1 | 1 | 3 | 1 | 1 |
| Mannitol | 1 | 1 | 5 | 1 | 1 |
| Sorbitol | 1 | 1 | 5 | 1 | 1 |
| α-methyl-D-mannoside | 1 | 1 | 1 | 1 | 1 |
| α-methyl-D-glucoside | 1 | 1 | 5 | 1 | 1 |
| N-acetyl-glucosamine | 5 | 1 | 4 | 4 | 3 |
| Amygdaline | 3 | 1 | 4 | 2 | 3 |
| Arbutin | 1 | 1 | 4 | 4 | 3 |
| Aesculin | 5 | 1 | 5 | 5 | 3 |
| Salicine | 2 | 1 | 4 | 4 | 3 |
| Cellobiose | 5 | 1 | 5 | 5 | 3 |
| Maltose | 5 | 4 | 3 | 1 | 5 |
| Lactose | 3 | 4 | 5 | 1 | 3 |
| Melibiose | 5 | 4 | 1 | 1 | 1 |
| Saccharose | 5 | 4 | 3 | 1 | 5 |
| Trehalose | 1 | 4 | 5 | 1 | 3 |
| Inulin | 1 | 1 | 1 | 1 | 1 |
| Melezitose | 1 | 1 | 5 | 1 | 1 |
| D-raffinose | 5 | 4 | 1 | 1 | 3 |
| Starch | 1 | 1 | 1 | 1 | 4 |
| Glycogen | 1 | 1 | 1 | 1 | 4 |
| Xylitol | 1 | 1 | 1 | 1 | 1 |
| β-gentiobiose | 4 | 1 | 3 | 3 | 2 |
| D-turanose | 1 | 1 | 5 | 1 | 3 |
| D-lyxose | 1 | 1 | 3 | 1 | 1 |
| D-tagarose | 2 | 1 | 5 | 4 | 1 |
| D-fucose | 1 | 1 | 1 | 1 | 1 |
| L-fucose | 1 | 1 | 1 | 1 | 1 |
| D-arabitol | 1 | 1 | 1 | 1 | 1 |
| L-arabitol | 1 | 1 | 1 | 1 | 1 |
| Gluconate | 1 | 3 | 2 | 1 | 1 |
| 2-keto-gluconate | 1 | 1 | 1 | 1 | 1 |
| 5-keto-gluconate | 1 | 1 | 1 | 1 | 1 |
| API rapid ID32s |  |  |  |  |  |
| Arginine dihydrolase | 1 | 5 | 1 | 5 | 1 |
| β-glucosidase | 5 | 1 | 5 | 3 | 1 |
| β-galactosidase (1) | 1 | 5 | 1 | 1 | 5 |
| β-glucuronidase | 1 | 1 | 1 | 1 | 1 |
| α-galactosidase | 5 | 3 | 1 | 1 | 1 |
| Alkaline phosphatase | 1 | 1 | 1 | 1 | 2 |
| Ribose | 1 | 5 | 5 | 5 | 1 |
| Mannitol | 1 | 1 | 5 | 1 | 1 |
| Sorbitol | 1 | 1 | 1 | 1 | 1 |
| Lactose | 1 | 5 | 1 | 1 | 1 |
| Trehalose | 1 | 5 | 5 | 1 | 3 |
| Raffinose | 5 | 1 | 1 | 1 | 2 |
| Acetoin | 5 | 5 | 5 | 5 | 1 |
| Alanine-phenylalanine-proline arylamidase | 5 | 1 | 4 | 3 | 5 |
| β-galactosidase (2) | 1 | 5 | 5 | 1 | 5 |
| Pyroglutamate | 4 | 1 | 5 | 1 | 1 |
| N-acetyl-β-glucosamine | 1 | 1 | 2 | 1 | 1 |
| Glycyl-tryptophan | 1 | 1 | 1 | 1 | 1 |
| Hippurate | 1 | 1 | 5 | 4 | 1 |
| Glycogen | 1 | 1 | 1 | 1 | 1 |
| Pullulan | 1 | 1 | 1 | 1 | 1 |
| Maltose | 2 | 5 | 1 | 1 | 5 |
| Melibiose | 5 | 1 | 1 | 1 | 1 |
| Melezitose | 1 | 1 | 2 | 1 | 1 |
| Sucrose | 5 | 5 | 1 | 1 | 5 |
| L-arabinose | 1 | 1 | 1 | 1 | 1 |
| D-arabitol | 1 | 1 | 1 | 1 | 1 |
| Methyl-β-D-glucopyranoside | 2 | 1 | 1 | 1 | 1 |
| Tagatose | 3 | 1 | 3 | 1 | 1 |
| β-mannosidase | 1 | 1 | 1 | 1 | 1 |
| Cyclodextrin | 1 | 1 | 1 | 1 | 1 |
| Urease | 1 | 1 | 1 | 1 | 1 |
| Hemolysis | 3 | 1 | 3 | 3 | 3 |

EXAMPLE 10

Characterisation of Bacterial Strains LN 40, LN 113, LN 99, LN 23, and LN 01 using Random Amplified Polymorphic DNA Furthermore, the bacterial strains were analysed with RAPD (Random Amplified Polymorphic DNA). This technique is described by, for instance, Williams, J G, et al, Nucl Acids Res, 18: 6531 (1990), and has previously been used not only to detect strain diversity, but also for gene mapping, population analyses, epidemiology and to analyse taxonomic and phylogenetic relationships (Welsh, J, et al, PCR 2: A Practical Approach, McPherson, M J, Hames, B D, and Taylor, G R, eds Chapter 11, IRL Press (1995).

Reproducible arrays of strain specific products were generated using a short oligonucleotide primer (5'ACGCGCAAC 3') under low stringency condition in PCR (Polymerase Chain Reaction). The resulting arrays were thereafter analysed by gel electrophoresis, and compared to type strains of each bacterial species, which had been subjected to the same treatment.

Figure 2:
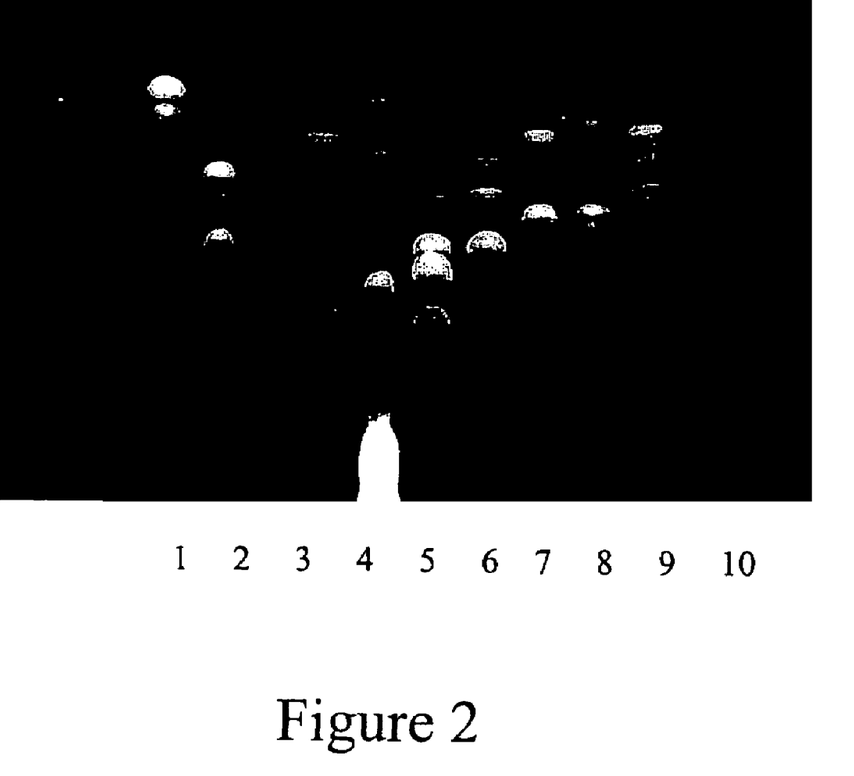
FIG. 2 shows a picture of a gel with strain specific products generated using RAPD and gel electrophoresis. Strains LN 40, LN 99, LN 113, LN 01 and LN 23, respectively, are compared to type strains of the respective bacterial species.

The results from this analysis are summarized in FIG. 2.
Lane 1 is $L\ fermentum$, ATCC $14931^T$,
lane 2 is LN 99,
lane 3 is $L\ crispatus$, CCUG $44117^T$,
lane 4 is LN 01,
lane 5 is a 100 bp molar weight marker,
lane 6 is LN 23,
lane 7 is LN 40,
lane 8 is $L\ gasseri$, ATCC $19992^T$,
lane 9 is LN 113, and
lane 10 is $L\ casei$ ATCC $4646^T$.

In FIG. 2, major differences between the bacterial strains according to the present invention (LN 40, LN 113, LN 99, LN 23, and LN 01) and the respective type strains can be seen.

The present invention also relates to a composition for prophylaxis and/or treatment of infections of the urogenital tract, comprising at least one of said bacterial strains (LN 40, LN 113, LN 99, LN 01, and LN 23).

Preferably, the composition comprises all said strains, i e strain LN 40, strain LN 113, strain LN 99, strain LN 01, and strain LN 23.

The composition is preferably formulated for vaginal administration, such as a suppository, capsule, pills, tablet, suspension, spray, gel, cream, powder, or any other form of vaginal insert, which may comprise conventional pharmaceutical excipients used in the art. Additionally, the present invention describes a sanitary article, such as feminine absorbent products (e g tampons, sanitary napkins, panty liners, e t c), diapers, and incontinence guards, for prophylaxis and/or treatment of infections of the urogenital tract comprising at least one of said bacterial strains (LN 40, LN 113, LN 99, LN 01, and LN 23).

Preferably, the sanitary article comprises all said strains, i e strain LN 40, strain LN 113, strain LN 99, strain LN 01, and strain LN 23.

The sanitary article is preferably a tampon.

Furthermore, the present invention describes the use of at least one of said bacterial strains (LN 40, LN 113, LN 99, LN 01, and LN 23) for the production of a composition or a sanitary article for prophylaxis and/or treatment of infections of the urogenital tract, preferably bacterial vaginosis or any other bacterial disorder in the vagina.

Moreover, the present invention describes a method for prophylaxis and/or treatment of infections of the urogenital tract, preferably bacterial vaginosis or any other bacterial disorder in the vagina, wherein at least one of said bacterial strains (LN 40, LN 113, LN 99, LN 01, and LN 23) is vaginally administered in a therapeutically effective amount to prevent, alleviate the effects of, and/or treat a microbial infection. The bacterial strains are preferably administered using a vaginal formulation and/or a sanitary article, most preferably a tampon.

In summary, the bacterial strains LN 40, LN 113, LN 99, LN 01, and LN 23 show excellent properties with regard to:
- ability to inhibit growth of uropathogens (including a rapid bacterial growth)
- ability to colonise and establish in vivo upon vaginal administration, even during menstrual discharge,
- stability of bacterial viability upon lyophilisation and over longer periods of storage (shelf life), and
- preservation of genetic profile upon repeated cultivation and in vivo.

Furthermore, these bacterial strains are also favourable in view of economical aspects.

Altogether, these properties imply that the bacterial strains according to the present invention are very well suited for industrial large-scale production of a consumption product (such as a composition or sanitary article) comprising said bacterial strains for preventing, alleviating the effects of, and/or treating a microbial infection of the urogenital tract.

While the invention has been described in detail and with reference to specific embodiments thereof, it will be apparent for one skilled in the art that various changes and modifications can be made therein without departing from the spirit and scope thereof.

The invention claimed is:

1. An isolated bacterial strain of the genus *Lactobacillus* or *Pediococcus* selected from the group consisting of the strain of *Lactobacillus gasseri*, LN 40, deposited under number LMG P-20560, the strain of *Lactobacillus casci* subsp *rhamnosus*, LN 113, deposited under number LMG P-20562, the strain of *Lactobacillus fermentum*, LN 99, deposited under number LMG P-20561, the strain of *Lactobacillus crispatus*, LN 01, deposited under number LMG P-20558, and the strain of *Pediococcus acidilactici*, LN 23, deposited under number LMG P-20559, and having the ability to colonise and become established in a human vagina upon vaginal administration during menstrual discharge, said strains were deposited at Belgian Coordinated Collections of Microorganisms on 14 Jun. 2001.

2. A composition for treatment of infections of the urogenital tract, comprising at least one of the bacterial strains according to claim 1.

3. A composition according to claim 2 formulated for vaginal administration.

4. A sanitary article for treatment of infections of the urogenital tract, comprising at least one of the bacterial strains according to claim 1.

5. The sanitary article according to claim 4, in the form of a tampon.

6. A sanitary article according to claim 4 for treatment of bacterial vaginosis or any other bacterial disorder in the vagina.

* * * * *